United States Patent [19]
Javitt

[11] Patent Number: 5,918,208
[45] Date of Patent: *Jun. 29, 1999

[54] SYSTEM FOR PROVIDING MEDICAL INFORMATION

[75] Inventor: Jonathan C. Javitt, Chevy Chase, Md.

[73] Assignee: Ingenix, Inc., Minnetonka, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/422,511

[22] Filed: Apr. 13, 1995

[51] Int. Cl.$^6$ .......................... G06F 159/00; G06F 17/60
[52] U.S. Cl. ..................................... 705/2; 705/7; 705/10
[58] Field of Search ............................... 364/401 R, 406, 364/401 M; 395/600, 202, 203, 207, 210; 705/1, 2, 3, 4, 7, 8, 10; 735/376

[56] References Cited

U.S. PATENT DOCUMENTS

| | | | |
|---|---|---|---|
| 5,070,452 | 12/1991 | Doyle, Jr. et al. | 364/401 |
| 5,136,502 | 8/1992 | Van Remortel et al. | 364/413.01 |
| 5,191,522 | 3/1993 | Bosco et al. | 364/401 R |
| 5,253,164 | 10/1993 | Holloway et al. | 364/406 |
| 5,307,262 | 4/1994 | Ertel | 364/413.01 |
| 5,325,293 | 6/1994 | Dorne | 364/413.01 |
| 5,327,341 | 7/1994 | Whalen et al. | 364/413.01 |
| 5,406,477 | 4/1995 | Harhen | 364/578 |
| 5,446,885 | 8/1995 | Moore et al. | 395/600 |
| 5,483,443 | 1/1996 | Milstein et al. | 395/203 |
| 5,486,999 | 1/1996 | Mebane | 395/202 |
| 5,508,912 | 4/1996 | Schneiderman | 364/401 R |
| 5,524,645 | 6/1996 | Wills | 128/898 |
| 5,557,514 | 9/1996 | Seare et al. | 395/202 |

OTHER PUBLICATIONS

Hallan, J.B. et al.: Analysis of Insurance Benefits Plans for Alcoholism Treatment Through Computer Simulation: Comp in Psychiatry/Psychology, vol. 8, No. 2, pp. 12–14, Summer 1987; Dialog File 2, #02979117.

Author Unknown: "Health Risk Management—Business Strategy" Nov. 3, 1990, Dialog File 16, # 02869121.

Fontaine, et al.: "Evaluation of Diagnostic Technologies . . . " Ann. Meet. Int. Soc. Technol. Assess Health Care, 1995, 11 p. Abstract No. 169, Dialog 151, # 02874620.

Miller & Luft: "Estimating Health Expenditure Growth Under Managed Competition . . . ", Dialog File 148, Acc. # 07714167, Journal of Amer. Med. Assoc. (JAMA) vol. 273, No. 8, p. 656 [19 pages sent].

*Primary Examiner*—Joseph Thomas
*Attorney, Agent, or Firm*—Merchant, Gould, Smith, Edell, Welter & Schmidt, P.A.

[57] ABSTRACT

A managed care expert system provides a graphical, interactive computer system which accepts user input relating to contract variables for a plurality of alternative contract scenarios, consults a database of national and locality-specific utilization data, performs a utilization and revenue analysis for both commercial and Medicare-age beneficiaries, and provides a synthetic fee schedule for comparing the likely revenue under capitation for a plurality of services to revenue for those services under a current reimbursement scenario. The system of the invention in its preferred embodiment enables a physician or other health care professional to use a broad array of assumptions to forecast utilization of medical procedures and estimated revenue per procedure under multiple capitation scenarios.

11 Claims, 7 Drawing Sheets

Microfiche Appendix Included
(4 Microfiche, 310 Pages)

Utilization

| Procedure | Current | -10% | -20% | -40% |
|---|---|---|---|---|
| Office visits | 0.584 | 0.526 | 0.466 | 0.351 |
| Cataract surgery | 0.038 | 0.034 | 0.031 | 0.023 |
| Neodymium-YAG capsulotomy | 0.018 | 0.017 | 0.015 | 0.011 |
| Visual field testing | 0.050 | 0.045 | 0.040 | 0.030 |
| Laser trabeculoplasty | 0.005 | 0.005 | 0.004 | 0.003 |
| Retinal photocoagulation | 0.003 | 0.003 | 0.002 | 0.002 |

FIG. 1

RVU per Covered Life Year

| Procedure | RVU | Current | -10% | -20% | -40% |
|---|---|---|---|---|---|
| Office visits | 1.37 | 0.79 | 0.72 | 0.64 | 0.48 |
| Cataract surgery | 27.07 | 1.02 | 0.92 | 0.81 | 0.61 |
| Neodymium-YAG capsulotomy | 9.14 | 0.17 | 0.15 | 0.13 | 0.10 |
| Visual field testing | 0.78 | 0.04 | 0.04 | 0.03 | 0.02 |
| Laser trabeculoplasty | 14.07 | 0.07 | 0.06 | 0.00 | 0.00 |
| Retinal photocoagulation | 19.19 | 0.06 | 0.09 | 0.00 | 0.00 |
| Total per Beneficiary | | 2.71 | 2.47 | 2.20 | 1.65 |

FIG. 2

| Procedure | Expected Revenue, $ | | | |
|---|---|---|---|---|
| | Current | -10% | -20% | -40% |
| Office visits | 39 | 43 | 49 | 65 |
| Cataract surgery | 780 | 855 | 962 | 1282 |
| Neodymium-YAG capsulotomy | 263 | 289 | 325 | 433 |
| Visual field testing | 22 | 25 | 28 | 37 |
| Laser trabeculoplasty | 405 | 444 | 500 | 666 |
| Retinal photocoagulation | 553 | 606 | 682 | 909 |

FIG. 7

| Category | Number of Procedures | |
| --- | --- | --- |
| | <65 | 65+ |
| Extracapsular extraction/IOL | 6659 | 1198580 |
| Intracapsular extraction/IOL | 1176 | 15000 |
| Secondary IOL implants | 242 | 29940 |
| Capsulotomy | 1593 | 577520 |
| Glaucoma Surgery (incisional) | 505 | 61380 |
| Glaucoma Surgery (laser) | 1388 | 223340 |
| Diabetes related surgery and laser | 3606 | 236600 |
| Retinal detachment surgery | 557 | 29080 |
| Vitreous procedures | 424 | 51840 |
| Other retinal procedures | 638 | 24880 |
| Lacrimal non-tumor procedure | 1817 | 112440 |
| Conjunctival procedures | 432 | 7540 |
| Lid non-tumor, non-traum procedure | 4529 | 213720 |
| Enucleation | 77 | 2440 |
| Scleral procedures | 333 | 1580 |

FIG. 8

| Category | Current Utilization | | Scenario 1 | | Scenario 2 |
|---|---|---|---|---|---|
| | <65 | 65+ | <65 | 65+ | <65 |
| Extracapsular extraction/IOL | 0.00264 | 0.03828 | 0.00264 | 0.03828 | 0.00264 |
| Intracapsular extraction/IOL | 0.00047 | 0.00048 | 0.00047 | 0.00048 | 0.00047 |
| Secondary IOL implants | 0.00010 | 0.00096 | 0.00010 | 0.00096 | 0.00010 |
| Capsulotomy | 0.00063 | 0.01844 | 0.00063 | 0.01844 | 0.00063 |
| Glaucoma Surgery (incisional) | 0.00020 | 0.00196 | 0.00020 | 0.00196 | 0.00020 |
| Glaucoma Surgery (laser) | 0.00055 | 0.00713 | 0.00055 | 0.00713 | 0.00055 |
| Diabetes related surgery and laser | 0.00143 | 0.00756 | 0.00143 | 0.00756 | 0.00143 |
| Retinal detachment surgery | 0.00022 | 0.00093 | 0.00022 | 0.00093 | 0.00022 |
| Vitreous procedures | 0.00017 | 0.00166 | 0.00017 | 0.00166 | 0.00017 |
| Other retinal procedures | 0.00025 | 0.00079 | 0.00025 | 0.00079 | 0.00025 |
| Lacrimal non-tumor procedure | 0.00072 | 0.00360 | 0.00072 | 0.00360 | 0.00072 |
| Conjunctival procedures | 0.00017 | 0.00024 | 0.00017 | 0.00024 | 0.00017 |
| Lid non-tumor, non-traum procedure | 0.00179 | 0.00683 | 0.00179 | 0.00683 | 0.00179 |
| Enucleation | 0.00003 | 0.00008 | 0.00003 | 0.00008 | 0.00003 |
| Scleral procedures | 0.00013 | 0.00005 | 0.00013 | 0.00005 | 0.00013 |

FIG. 9

| CPT Code | Current Utilization | | Scenario 1 | | Scenario 2 |
|---|---|---|---|---|---|
| | <65 | 65+ | <65 | 65+ | <65 |
| 65820 | 0.00000 | 0.00001 | 0.00000 | 0.00001 | 0.00001 |
| 65850 | 0.00001 | 0.00006 | 0.00001 | 0.00006 | 0.00006 |
| 66150 | 0.00001 | 0.00003 | 0.00001 | 0.00003 | 0.00003 |
| 66155 | 0.00001 | 0.00003 | 0.00001 | 0.00003 | 0.00003 |
| 66160 | 0.00001 | 0.00011 | 0.00001 | 0.00011 | 0.00011 |
| 66165 | 0.00000 | 0.00000 | 0.00000 | 0.00000 | 0.00000 |
| 66170 | 0.00011 | 0.00137 | 0.00011 | 0.00137 | 0.00137 |
| 66500 | 0.00000 | 0.00001 | 0.00000 | 0.00001 | 0.00001 |
| 66505 | 0.00000 | 0.00000 | 0.00000 | 0.00000 | 0.00000 |
| 66625 | 0.00004 | 0.00030 | 0.00004 | 0.00030 | 0.00030 |
| 66630 | 0.00000 | 0.00002 | 0.00000 | 0.00002 | 0.00002 |
| 66700 | 0.00001 | 0.00001 | 0.00001 | 0.00001 | 0.00001 |
| 66720 | 0.00000 | 0.00001 | 0.00000 | 0.00001 | 0.00001 |
| 66740 | 0.00000 | 0.00000 | 0.00000 | 0.00000 | 0.00000 |

| Category | RVU Value | RVU Per Beneficary <65 | 65+ |
|---|---|---|---|
| Extracapsular extraction/IOL | 27.05 | 0.07140 | 1.03535 |
| Intracapsular extraction/IOL | 20.35 | 0.00956 | 0.00977 |
| Secondary IOL implants | 19.87 | 0.00199 | 0.01908 |
| Capsulotomy | 9.14 | 0.00576 | 0.16854 |
| Glaucoma Surgery (incisional) | 22.01 | 0.00440 | 0.04315 |
| Glaucoma Surgery (laser) | 13.59 | 0.00747 | 0.09687 |
| Diabetes related surgery and laser | 21.43 | 0.03065 | 0.16203 |
| Retinal detachment surgery | 33.18 | 0.00728 | 0.03078 |
| Vitreous procedures | 30.28 | 0.00515 | 0.05027 |
| Other retinal procedures | 14.52 | 0.00363 | 0.01147 |
| Lacrimal non-tumor procedure | 3.31 | 0.00238 | 0.01191 |
| Conjunctival procedures | 4.62 | 0.00079 | 0.00111 |

FIG. 12

Expected RVU Per Beneficary - CPT Codes

| Category | RVU Value | RVU Per Beneficary <65 | 65+ |
|---|---|---|---|
| 66821 | 9.09000 | 0.00554 | 0.01832 |
| 66830 | 16.05000 | 0.00032 | 0.00012 |

FIG. 13

| Category | Revenue Per Service | |
| --- | --- | --- |
| | <65 | 65+ |
| Extracapsular extraction/IOL | 0.00 | 0.00 |
| Intracapsular extraction/IOL | 0.00 | 0.00 |
| Secondary IOL implants | 0.00 | 0.00 |
| Capsulotomy | 0.00 | 0.00 |
| Glaucoma Surgery (incisional) | 0.00 | 0.00 |
| Glaucoma Surgery (laser) | 0.00 | 0.00 |
| Diabetes related surgery and laser | 0.00 | 0.00 |
| Retinal detachment surgery | 0.00 | 0.00 |
| Vitreous procedures | 0.00 | 0.00 |
| Other retinal procedures | 0.00 | 0.00 |
| Lacrimal non-tumor procedure | 0.00 | 0.00 |
| Conjunctival procedures | 0.00 | 0.00 |
| Lid non-tumor, non-traum procedure | 0.00 | 0.00 |

FIG. 14

| CPT Code | Revenue Per Service | |
| --- | --- | --- |
| | <65 | 65+ |
| 66821 | 0.00 | 0.00 |
| 66830 | 0.00 | 0.00 |

SYSTEM FOR PROVIDING MEDICAL INFORMATION

This application includes a microfiche appendix which has a total of four microfiche and a total of 310 frames.

BACKGROUND OF THE INVENTION

1. Field of the Invention

The invention relates in general to computer-based tools for aiding in business and financial decision-making, and in particular to a novel system for aiding a physician or other interested party in making decisions relating to contracts between health care payers and physician contractors or other health care providers.

2. Background and Related Art

Capitated health care is rapidly gaining market acceptance in many geographical areas. This environment raises many decisional challenges for the physician and administrators in the medical care field. In particular, physicians and medical practice administrators entering into capitated contracts have had difficulty in balancing the often-conflicting goals of maintaining standards of quality in health care delivery and maintaining adequate practice revenue. One of the principal difficulties encountered in this regard has been the lack of an accurate means for comparing revenues generated under an at-risk contract with those generated under a traditional fee-for-service arrangement. Specifically, difficulty has arisen in understanding the interactions between an amount paid under a capitated contract, the utilization of services under the contract, and the resulting revenue earned in delivering those services.

SUMMARY OF THE INVENTION

It is therefore an object of the invention to provide a computer-based system for comparing revenues and costs generated under an at-risk contract with those generated under a traditional fee-for-service arrangement.

It is a further object of the invention to provide a computer-based system for demonstrating to a user the interactions between an amount paid under a capitated contract, the utilization of services under the contract, and the resulting revenue earned in delivering those services.

In a preferred embodiment, the invention provides a graphical, interactive computer system which accepts user input relating to contract variables for a plurality of alternative contract scenarios, consults a database of national and locality-specific utilization data, performs a utilization and revenue analysis for both commercial and Medicare-age beneficiaries, and provides a synthetic fee schedule for comparing the likely revenue and costs under capitation for a plurality of services to revenue for those services under a current reimbursement scenario. The system of the invention in its preferred embodiment enables a physician to use a broad array of assumptions to forecast utilization of medical procedures and estimated revenue per procedure under multiple capitation scenarios.

BRIEF DESCRIPTION OF THE DRAWINGS

The foregoing and other objects, features, and advantages of the invention will be apparent from the following more particular description of preferred embodiments as illustrated in the accompanying drawings in which reference characters refer to the same parts throughout the various views. The drawings are not necessarily to scale, emphasis instead being placed upon illustrating principles of the invention.

FIG. 1 is a table illustrating the utilization of selected procedures under alternative scenarios.

FIG. 2 is a table illustrating expected Relative Value Units (RVUs) per beneficiary based on the table of FIG. 1.

FIG. 7 is a view of a graphical "Procedures Provided" screen created by the machine of the invention.

FIG. 8 is a view of a graphical "Summary" screen created by the machine of the invention.

FIG. 9 is a view of a graphical "Utilization of Procedures" screen created by the machine of the invention.

FIG. 10 is a view of a graphical "Utilization of Procedures—CPT Codes" screen created by the machine of the invention.

FIG. 11 is a view of a graphical "Expected RVU Per Beneficiary" screen created by the machine of the invention.

FIG. 12 is a view of a graphical "Expected RVU Per Beneficiary—CPT Codes" screen created by the machine of the invention.

FIG. 13 is a view of a graphical "Revenue" screen created by the machine of the invention.

FIG. 14 is a view of a graphical "Revenue—CPT Codes" screen created by the machine of the invention.

DETAILED DESCRIPTION OF THE DRAWINGS

Figures 3, 4:
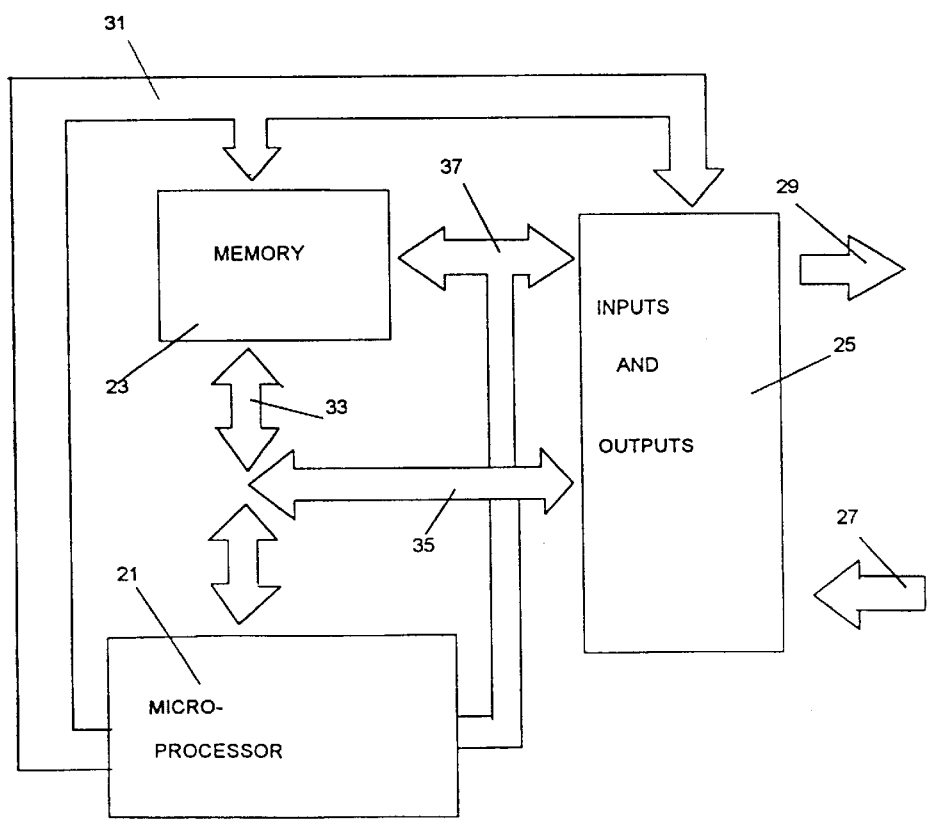
FIG. 3 is a table illustrating expected revenue per procedure based on the data in the table of FIG. 2.
FIG. 4 illustrates a schematic block diagram of a typical computer used to implement the invention.

FIGS. 1 through 3 set forth a model illustrating the underlying theory which is put into practice by the machine of the invention. The model is based on all medical/surgical services likely to be provided to a Medicare beneficiary in the field of ophthalmology. It will be understood by those skilled in the art, however, that the analysis shown in the figures, and the machine of the invention, can be applied to any medical specialty or all medical services. The basic premise is that a defined "basket" of services is likely to be provided to a group of patients over the course of a year. For instance, if 1000 beneficiaries make 584 office visits under current utilization, the likelihood of any one person making an office visit is 0.584.

FIG. 1 depicts the utilization of commonly performed procedures under Medicare indemnity patterns, compared with what might be observed if utilization were decreased by a uniform amount. The "Current" utilization column reflects the probability of a Medicare beneficiary undergoing a particular procedure in 1991, based on national averages, while the remaining three columns represent scenarios wherein utilization of all procedures is 10%, 20% or 40% lower as compared to current utilization. In reality, utilization of some services might be deliberately increased. For instance, one might deliberately increase utilization of eye examination and photocoagulation of patients with diabetes with the expectation that fewer endolaser vitrectomies will be needed.

FIG. 2 illustrates the expected Relative Value Units (RVUs) per beneficiary (for a Covered Life Year, or "CLY") for the procedures shown in FIG. 1. Expected procedure-specific and total RVUs can be derived by multiplying the utilization for each procedure (from FIG. 1) by the RVU value for that procedure under each utilization scenario. By converting procedures to RVU values and multiplying those values by the likelihood that a beneficiary will undergo a procedure in a particular year, it is possible to estimate the amount of professional service likely to be provided. Of course, these values hold only for large groups of people, and an individual may use more or less care.

As shown in FIG. 3, using the above inputs one can project the revenue per service, based on the per-member-per-month (PMPM) capitation amount. The capitation rate chosen ($6.50) is an approximate contract price that has been reported for Medicare at-risk contracts in mature managed-care markets. Capitation rates considerably higher and lower than this will have obvious effects on total revenue and revenue per RVU. In contrast to a fee-for-service arrangement, in which the fee represents that actual amount paid for a given service, independent of utilization, this projected revenue represents the portion of the total capitation revenue that might be appropriately allocated to a given service at a particular level of utilization. With appropriate cost-accounting techniques, the estimated revenue per service can be compared with the actual cost of providing that service to determine profit or deficit. The revenue per service (FIG. 3) is calculated as follows: The total capitation amount (PMPMX12) is divided by total RVU per beneficiary (FIG. 2) to yield an expected revenue per RVU. The expected revenue per RVU is multiplied by the RVU value for each procedure.

The expected revenue per procedure does not include any copayment or coinsurance, which may constitute a meaningful portion of revenue, particularly in an office visit. Although there are known imperfections in the RVU scale, the effect of those imperfections would be to overestimate the revenue associated with some procedures and to underestimate the revenue associated with others. While this might lead to erroneous calculation of profit or loss associated with the performance of any individual procedure, it would have no effect on overall reimbursement, since, by definition, that is fixed. Others who apply this method may wish to adjust the RVU scale based on their own information, and such adjustments are discussed below in the description of the machine according to the invention.

As shown in the model, revenue per procedure under capitated care is likely to be lower than current fee schedules if utilization is maintained at current levels. There are some offsetting factors, such as substantial reductions in billing and collection, more stable cash flow, and minimal bad debt. Equally apparent is that lower utilization rapidly translates into higher projected revenues per service. The problem is not whether one can decrease utilization to the point where capitated care becomes financially attractive, but rather what mechanisms of monitoring process and outcomes of care must be in place to inform the physician and safeguard the patient.

Turning now to a discussion of the preferred embodiment of the invention, the invention includes a machine comprising a computer system, operating pursuant to software, that produces a series of screens for permitting a user to create, select, and display information relating to managed care decision-making. As shown in FIG. 4, a microprocessor 21 receives input information 27 from I/O 25, which may comprise a keyboard, a mouse, a data storage device, a display, and other known input/output devices. Microprocessor 21 also causes output information 29, such as a graphical or textual display, to flow therefrom. Timing and control signals 37 are transferred between I/O 25 and a memory 23. Instruction and data codes 33 flow between memory 23 and microprocessor 21; data codes 35 flow between I/O 25 and memory 23, as well as between I/O 25 and microprocessor 21; address codes 31 from microprocessor 21 flow to memory 23 and I/O 25.

As set forth above, the invention produces a series of graphical interactive screens which permit a user to create information relating to managed care decision-making. FIG. 4 issustrates a Main screen accordng to a preferred embodiment of the invention. The Main screen consists of boxes into with the user enters basic capitation assumptions in order to project utilization and revenue implications for a given capitation scenario. The user may specify three hypothetical scenarios, with different utilization and capitation rates for each, or may choose to keep one set of variables, such as utilization rate, constant while varying the others. Data are entered using the up and down arrows (either on a mouse or a keypad) in order to minimize data errors, such as misplaced decimal points, that are common when numbers are typed in by hand.

The "Utilization" rows on the Main screen allow a user to estimate the utilization under various capitation scenarios as it compares with indemnity insurance. Thus, a value of 100% means that the user is assuming utilization under capitation will be the same as under indemnity, while a value of 50% means that utilization under capitation is assumed to be half that of comparable beneficiaries under indemnity insurance. Utilization is specified for all office diagnostic services and for surgical service as separate entries.

While it is impossible to predict what utilization of ophthalmologic procedures is likely to be under any particular capitation plan, preliminary data have shown utilization experience under capitation that ranges from identical with indemnity to 40% below indemnity (Javitt J C. Early glimpses of capitated eye care. Arch Ophthalmol 112:887, 1994). It would be unreasonable to assume that utilization will automatically be lower than that under indemnity unless mechanisms, such as gatekeeper accountability, are in place. The possibility also exists that reduction in copayment that is often experienced when moving from indemnity to managed care plans may be associated with an increase in office visit utilization.

The "Capitation Rate" rows of the Main screen permit a user to enter the capitation rates for the machine of the invention to use in its calculations. Rates are preferably on a per-member-per-month basis, but it will be appreciated by those skilled in the art that other types of capitation rates, such as per-member-per-quarter, etc., could be used without departing from the spirit and scope of the invention.

The "Co-Pay" rows permit a user to enter copayments for the machine of the invention to use in its calculations. If a copayment is entered for office services, the copayment is generally applied once per visit. Thus, if two services are combined, such as a comprehensive eye examination and a visual field examination, the revenue per service for the second (and any additional) service will be overstated by the amount of the copayment.

A button bar appears along the tope of the Main screen. The buttons permit a user to access any of a series of sub-screens or dialog boxes for inputing and outputting information. The functions of these buttons and associated subscreens or dialog boxes will now be discussed.

Figure 6:
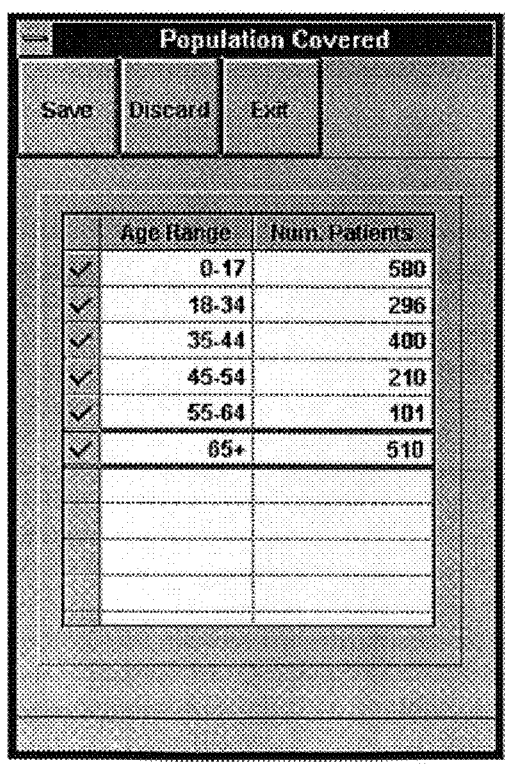
FIG. 6 is a view of a graphical "Population Covered" screen created by the machine of the invention.

A "Population" button accesses a "Population Covered" dialog box which is used to define the populations that are to be part of the analyses performed by the device of the invention. The Population Covered dialog box is shown in FIG. 6. A series of age ranges are listed in the dialog box, and a user enters, for each age range, the number of patients which are to be covered under a certain contract or potential contract scenario. Data entered is saved or discarded by clicking the appropriate button along the top of the Population Covered dialog box. An "Exit" button is can be actuated to return the user to the Main screen (FIG. 1).

A "Procedures" button on the Main screen (FIG. 5) is used to access a "Procedures Provided" dialog box, illustrated in FIG. 7. The Procedures Provided dialog box is used to select the ophthalmologic procedures that are to be part of the analyses performed by the device of the invention. A user can view the CPT code for a procedure double-clicking on the procedure.

By selecting certain procedures for inclusion, and observing the resulting effect on the outcome of the analyses (discussed in more detail below), a user can project the effect of being at-risk for all eyecare procedures versus being at-risk for sub-specialty procedures only. Procedures for which a health-care provider will not be responsible under a particular contract may be left out of the analysis by de-selecting the check boxes in the right-hand column of the Procedures Provided dialog box. If the analysis is to include certain procedures which are to be contracted out to other providers, those procedures should remain selected for inclusion; the Revenue dialog box, discussed in detail below, will provide insight into the amount that may be paid to other providers in a revenue-neutral manner.

There may also be situations in which providers are responsible only for subspecialty care, such as vitreo-retinal surgery. The machine of the invention may provide insight in this situation as well. However, the following caution applies. Currently, it is possible to estimate the number of surgical procedures to be performed in subspecialty areas but not to separate office visits by the same categories. Therefore, selecting only subspecialty procedure types and inputting a subspecialty capitation rate will estimate a revenue per procedure that includes all office visits, including visits for those persons who do not undergo a surgical procedure. It can be argued that all office visits with a given diagnosis (such as retinal detachment) be attributed to the associated surgical procedure.

A "Summary" button on the Main screen (FIG. 5) is used to access a "Summary" dialog box, which is illustrated in FIG. 8. The Summary dialog box displays a database of the number of procedures in aggregated categories for individuals under 65 and over 65. The Procedures dialog box provides a tabular display of data, including a "Category" column listing procedures, a "Number of Procedures column for patients under 65, and a "Number of Procedures" column for patients over 65.

A "Utilization" button on the Main screen (FIG. 5) accesses a Utilization-of-Procedures dialog box, which is illustrated in FIG. 9. The Utilization-of-Procedures dialog box permits a user to project the utilization of ophthalmologic procedures by beneficiary, under the utilization scenarios chosen on the Main screen. The default utilization rates are derived from a national or locality-specific database of rates observed for a particular year. Utilization is expressed as a simple rate. For instance, a rate of 0.050 means that 5 persons per 100 or 50 persons per thousand might undergo that procedure. Rates are based on the experience of beneficiaries from a particular locality who were covered by indemnity insurance in a particular year.

To view the utilization of procedures data by CPT code, a user can double-click on a particular procedure. Doing so accesses a "Utilization of Procedures—CPT Codes" dialog box, which is illustrated in FIG. 10.

An "RVU" button on the Main screen (FIG. 5) is used to access an "Expected RVU Per Beneficiary" dialog box, which is illustrated in FIG. 11. This dialog box is used to project the Relative Value Units (RVUs) of service associated with the categories of ophthalmologic service likely to provided under a particular contract or other scenario. RVU's of service are preferably obtained by multiplying the utilization rate of each procedure by its RVU value, as reflected in a Medicare Fee Schedule. A user can select which of the four scenarios (i.e., Current, Scenario 1, Scenario 2, or Scenario 3) to display by using a mouse to click one of the four buttons along the top of the screen.

While the use of relative value units to adjust payment rates across specialties is problematic because of difficulty of developing appropriate anchor procedures for comparison, the use of RVUs to compare one ophthalmologic procedure to another is less problematic, since the scale is based on answers provided by over 500 ophthalmologists.

To view the expected RVU data by CPT code, a user can double-click on a particular procedure. Doing so accesses an "Expectedd RVU Per Beneficiary—CPT Code" dialog box, which is illustrated in FIG. 12.

A "Revenue" button on the Main screen (FIG. 5) accesses a "Revenue" dialog box, which is illustrated in FIG. 13. The Revenue dialog box projects the revenue associated with each procedure under the scenario of Capitation Rate/Copayment/Utilization chosen by the user. The Revenue dialog box comprises a clumnar display of data, including a "Category" column listing procedures, a "Revenue Per Service" for patients under 65, and a "Revenue Per Service" column for patients over 65. While the revenue analysis illustrated in FIG. 13 has the appearance of a fee schedule, it is important to recognize the key difference, namely that predicted revenue will be underestimated if utilization is higher than expected and vice versa.

The invention according to the preferred embodiment predicts Revenue Per Service, as displayed in the Revenue dialog box, according to the following steps:

First, determine the total RVUs per procedure and per person likely to be provided under the chosen utilization scenario.

Second, calculate the Revenue ("R") per RVU as follows:

$$R \text{ per RVU} = (\text{Capitation Rate} \times 12)/\text{Total RVUs per person}$$

Third, calculate the Revenue Per Service ("RPS") as follows:

$$RPS = (\text{RVUs for service} \times \text{Revenue per RVU}) + \text{Copay}$$

The invention according to the preferred embodiment permits the user to choose to display revenue data for a particular scenario by selecting any of the "Current Utilization," "Scenario 1," "Scenario 2," or "Scenario 3" buttons along the top of the Revenue dialog box. A user may also view revenue data by CPT Code by double-clicking a particular procedure in the Category column. Doing so accesses a "Revenue—CPT Codes" dialog box, which is illustrated in FIG. 14.

A "Calculator" button on the Main screen (FIG. 5) accesses a "Capitation Calculator" dialog box, which is illustrated in FIG. 15. This dialog box permits use of the invention to perform ad hoc capitation calculations. A user selects Utilization and Co-Pay values by manipulating the various spin buttons in the top block of the Capitation Calculator dialog box. The user can then select an appropriate radio button for his preferred calculation method, i.e., Dollars Per RVU, Fee Schedule (Aggregate), or Fee Schedule (CPT Code). Selecting the "Calculate" button causes the invention to display a resulting capitation rate. The Capitation Calculator dialog box also preferably comprises three editor buttons: a "Utilization Editor" button, an "RVU Editor" button, and a "Fee Schedule Editor" button. The functions for each of the buttons are discussed below.

Figure 5:
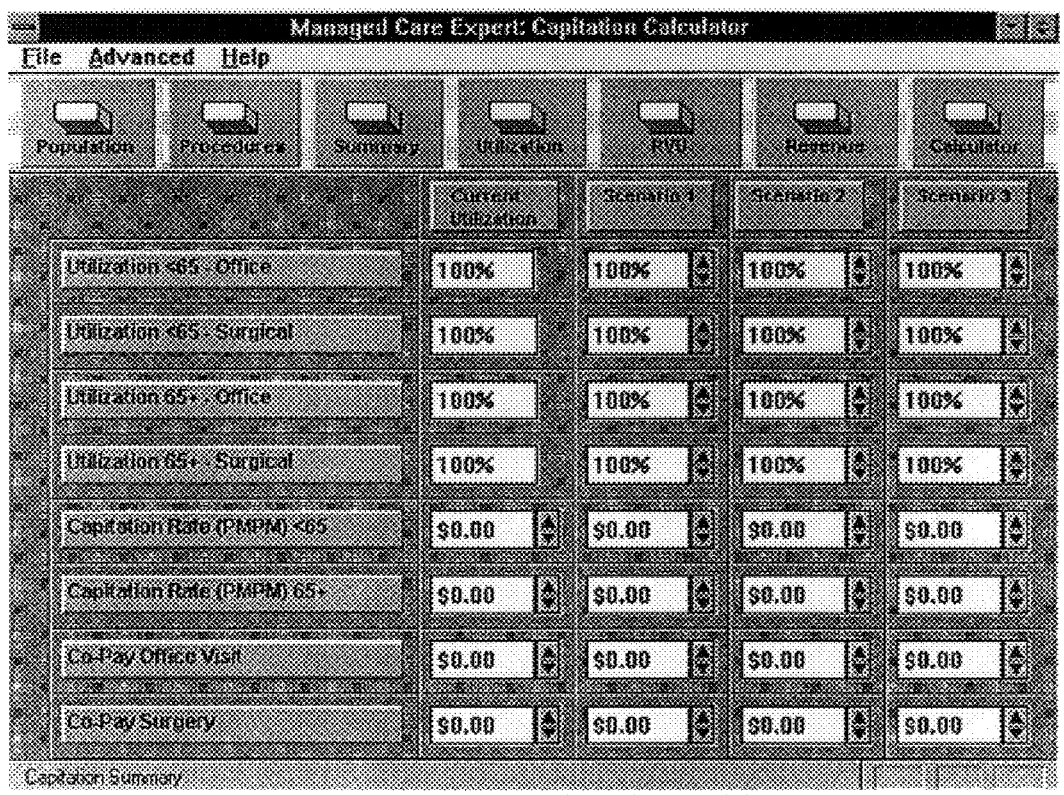
FIG. 5 is a view of a graphical "Main" screen created by the machine of the invention.

Selecting the "RVU Editor" button from the Capitation Calculator dialog box (FIG. 15) accesses an "RVU Editor" dialog box, which is illustrated in FIG. 16. The RVU Editor dialog box can also be accessed via an "Advanced" menu on the Main screen (FIG. 5). The RVU Editor function of the invention permits a user to enter and select user-defined RVU values. The RVU Editor dialog box comprises a tabular display of RVU data, including a Category column listing medical procedures, a "Default RVU" column listing widely-accepted default RVU values, and a "User Defined RVU" column in which a user can insert customized RVU values. A "Use Default" button causes the device of the invention to use the default database of RVU values for purposes of performing calculations, while a "Use Custom" button causes the device to use a database which includes the User-Defined RVU values.

The "Utilization Editor" button in the Capitation Calculator dialog box (FIG. 15) accesses a "Utilization Editor" dialog box, which is illustrated in FIG. 17. The Utilization Editor dialog box can also be accessed via the "Advanced" menu in the Main screen (FIG. 1). The default utilization rates used by the invention to perform calculations are based on a database of national or locality-specific values observed for a particular year. The Utilization Editor dialog box permits a user to enter user-defined utilization values to replace the default data. A "Use Default" button causes the invention to use the default database for calculations, while a "Use Custom" button causes the invention to use the customized utilization values defined by the user.

The "Fee Schedule Editor" button in the Capitation Calculator dialog box (FIG. 15) accesses an "Aggregate Editor—Medicare Fee Schedule" dialog box, which is illustrated in FIG. 18. The Aggregate Editor—Medicare Fee Schedule dialog box can also be accessed via the "Advanced" menu in the Main screen (FIG. 1). The default fee data used by the invention to perform calculations are based on a database which reflects the Medicare Fee Schedule for aggregated procedures. This dialog box permits a user to enter user-defined fees for aggregated procedures. A "Use Medicare" button causes the invention to use the default Medicare Fee Schedule database for calculations, while a "Use Custom" button causes the invention to use the customized fee data defined by the user. To view the fee data by CPT code, a user can double-click on a particular procedure. Doing so accesses a "CPT Editor—Medicare Fee Schedule" dialog box, which is illustrated in FIG. 19. This dialog box can also be accessed via the "Advanced" menu in the Main screen (FIG. 5).

The above-described "Advanced" menu further permits access to a "Locality Covered" dialog box, which is illustrated in FIG. 20. This dialog box permits a user to cause the machine of the invention to use alternate databases for its calculations so that the calculations use data drawn from a population which closely matches that of covered individuals for a particular contract scenario. A user may select a national database or one of a plurality of locality-specific databases. The localities available preferably are based on health market areas, using the Bureau of Economic Analysis Economic Areas, which correspond to standard Metropolitan Statistical Areas combined with their surrounding suburban and rural counties.

The above-described "Advanced" menu further permits access to a "User ID" dialog box, which permits a user to enter a name and identification number so as to permit use of the program by multiple, independent users. That is, a particular user's data is associated with his User Id information and can be recalled at a later time.

While the invention has been particularly shown and described with reference to a preferred embodiment thereof, it will be understood by those skilled in the art that various changes in form and details may be made therein without departing from the spirit and scope of the invention.

The embodiments of the invention in which an exclusive property or privilege is claimed are defined as follows:

1. A device for aiding in managed health care decision-making, comprising:
   means for selecting a plurality of medical procedures for analysis;
   means for storing a first database of health care utilization data indicating levels of utilization for said plurality of procedures under a first scenario;
   means for receiving user input of at least one variable affecting an amount of revenue derived from providing health care under a second scenario;
   means for creating, based at least in part upon said variable affecting revenue and data in said said first database, a second database of health care utilization data indicating levels of utilization for said plurality of procedures under said second scenario;
   means for projecting a first revenue amount relating to said first scenario, said first revenue amount being derived at least in part from said the data in said first database;
   means for projecting a second revenue amount relating to said second scenario, said second revenue amount being derived at least in part from said the data in said second database; and,
   means for displaying said first and second revenue amounts.

2. The device according to claim 1, wherein said at least one variable affecting revenue derived from providing health care comprises an indication of utilization under said second scenario.

3. The device according to claim 2, wherein at said indication of utilization under said second scenario comprises a percentage of a total utilization with respect to a corresponding total utilization under said first scenario.

4. The device according to claim 1, wherein said at least one variable affecting revenue derived from providing health care comprises a capitation rate reflecting a level of compensation under said second scenario.

5. The device according to claim 1, wherein said at least one variable affecting revenue derived from providing health care comprises an amount of co-payment under said second scenario.

6. The device according to claim 1, wherein said first database of health care utilization data comprises data for a specific geographic region, and wherein said first database is selected from a larger database comprising utilization data for a plurality of geographic regions.

7. The device according to claim 1, wherein said first scenario comprises a health care indemnity insurance scenario and said second scenario comprises a managed care plan scenario.

8. The device according to claim 1, wherein said first scenario comprises a first managed care plan scenario and said second scenario comprises a second managed care plan scenario.

9. A device for aiding in managed care decision-making, comprising:

means for selecting a plurality of medical procedures for analysis;

means for storing a database of health care utilization data indicating levels of utilization for a plurality of procedures;

means for receiving user input of at least one desired revenue amount for insuring provision of said plurality of procedures to a population;

means for calculating, based at least upon said data in said database and said at least one desired revenue amount, a capitation rate reflecting a level of compensation statistically required to achieve said desired revenue amount; and, means for displaying said capitation rate.

10. A device for aiding in managed health care decision-making, comprising:

means for selecting a plurality of medical procedures for analysis;

means for storing a first database of health care utilization data indicating levels of utilization for said plurality of procedures under a first scenario;

means for receiving user input of at least one variable affecting revenue derived from providing health care under a second scenario;

means for creating, based at least in part upon said variable affecting revenue and data in said said first database, a second database of health care utilization data indicating levels of utilization for said plurality of procedures under said second scenario;

means for displaying said second database of health care utilization data indicating levels of utilization for said plurality of procedures under said second scenario.

11. A device for aiding in managed health care decision-making, comprising:

means for selecting a plurality of medical procedures for analysis;

means for storing a first database of health care utilization data indicating levels of utilization for said plurality of procedures under a first scenario;

means for receiving user input of at least one variable affecting revenue derived from providing health care under a second scenario;

means for creating, based at least in part upon said variable affecting revenue and data in said said first database, a second database of health care utilization data indicating levels of utilization for said plurality of procedures under said second scenario;

means for storing a third database of data representing relative value units for each of said plurality of medical procedures;

means for creating a fourth database of relative-value-units-per-service based at least in part upon said data in said second database and said data in said third database.

* * * * *